United States Patent [19]
Kell

[11] 4,411,603
[45] Oct. 25, 1983

[54] DIAPHRAGM TYPE BLOOD PUMP FOR MEDICAL USE

[75] Inventor: Michael J. Kell, Decatur, Ga.

[73] Assignee: Cordis Dow Corp., Miami, Fla.

[21] Appl. No.: 276,752

[22] Filed: Jun. 24, 1981

[51] Int. Cl.³ .................. F04B 43/02; A61M 5/00
[52] U.S. Cl. ...................... 417/479; 128/DIG. 12; 137/855; 604/153
[58] Field of Search .................. 417/479, 560; 128/214 F, 214 G, DIG. 12; 137/855, 856; 604/153, 247

[56] References Cited

U.S. PATENT DOCUMENTS

| | | | |
|---|---|---|---|
| 2,378,613 | 6/1945 | Young et al. | 137/855 |
| 3,058,140 | 10/1962 | Henss | 417/566 X |
| 3,145,659 | 8/1964 | Svendsen | 417/479 X |
| 3,514,231 | 5/1970 | Belden | 137/855 X |
| 3,610,698 | 10/1971 | Gachot | 137/856 X |
| 3,802,807 | 4/1974 | Kilayko | 417/435 X |
| 4,051,852 | 10/1977 | Villari | 128/214 G X |

FOREIGN PATENT DOCUMENTS 2639992 3/1978 Fed. Rep. of Germany ... 128/214 F

*Primary Examiner*—Richard E. Gluck
*Attorney, Agent, or Firm*—Neal A. Waldrop; Jay C. Taylor

[57] ABSTRACT

A positive displacement pump for delivery of blood, or the like, from patients to an extracorporeal circuit, for purification, as in hemodialysis treatments. The pump is small, and sufficiently inexpensive to be discarded after one use. The pump comprises a single blood chamber attached to inlet and outlet conduits separated from the chamber and each other by low resistance flapper valves. The flapper valves are integral with a flexible diaphragm which forms one side of the blood chamber and are operative to close the outlet valve and to open the inlet valve to fill the blood cavity responsive to withdrawal of the diaphragm from the blood chamber cavity and to reverse each valve upon penetration of the diaphragm into the blood chamber to deliver uniformly small increments of blood to an artificial kidney or other blood treatment device.

9 Claims, 20 Drawing Figures

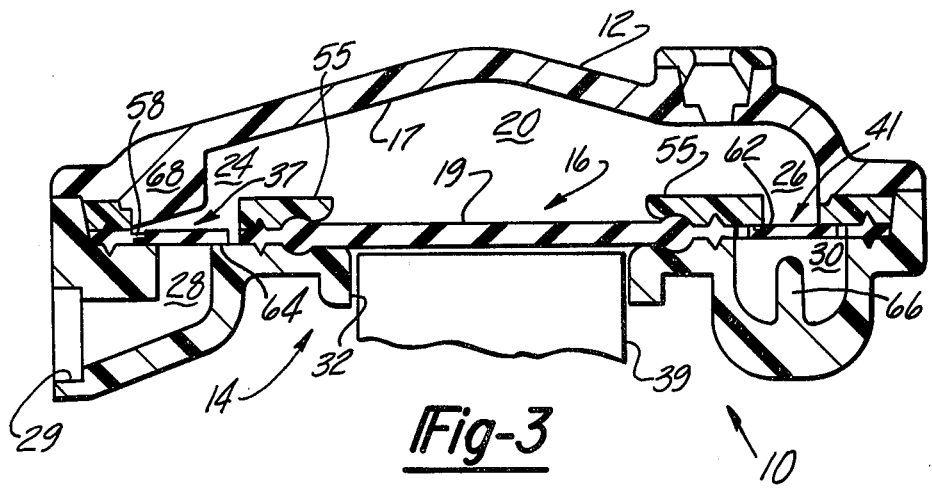
Fig-3
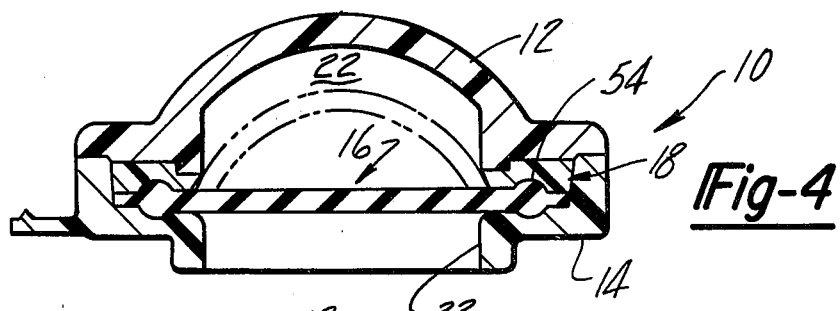
Fig-4
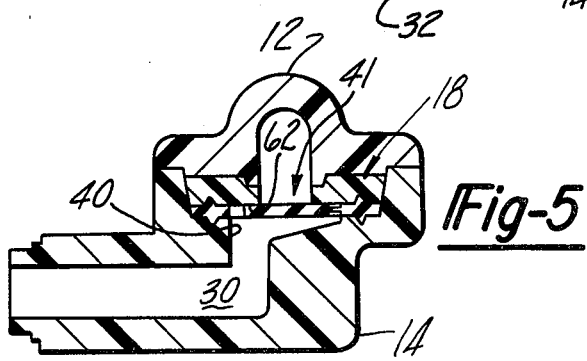
Fig-5
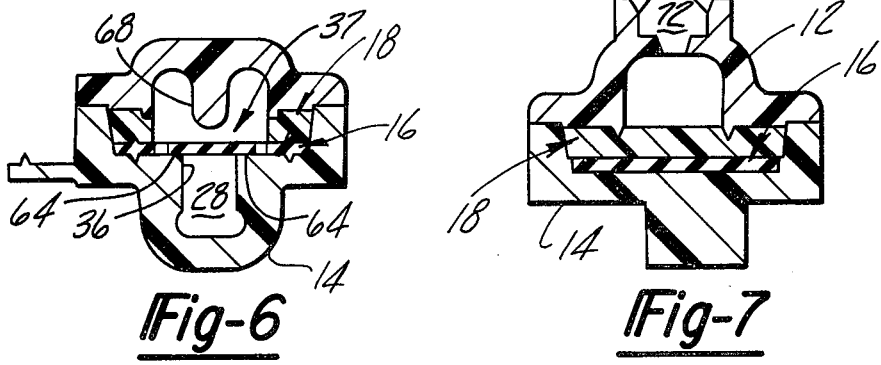
Fig-6
Fig-7

DIAPHRAGM TYPE BLOOD PUMP FOR MEDICAL USE

BACKGROUND OF THE INVENTION

This invention relates to a blood pump which employs diaphragm reciprocation into and from a blood chamber to propel blood through an extracorporeal circuit. In the past roller pumps have been used predominantly to assist blood flow in blood purification treatments outside the body. Such roller pumps usually comprise a length of blood tubing arranged in a generally circular arc and propel blood forward in slowly repetitive pulses as the roller compresses the tubing during rotation. Such peristaltic type pumps are satisfactory but do not readily lend themselves to adaptation and use with improved one-piece integral hollow fiber artificial kidneys of the type shown in U.S. Pat. No. 4,231,871.

Those familiar with current hemodialysis clinical usage of artificial kidneys and apparatus for controlling extracorporeal blood circulation during blood purification treatments or the like have long been aware of the desirability of providing a reliable blood pump fabricated sufficiently inexpensively such that the pump could be integrated with an artificial kidney and discarded along with the kidney after use.

The blood pump of this invention fills this need and provides a blood pump particularly suited for incorporation as an integral element into a hollow fiber artificial kidney of the type shown in U.S. Pat. No. 4,231,871. The pump of this invention is a small, lightweight single blood chamber equipped with a flexible diaphragm and inlet and outlet low resistance valves which alternately connect the blood chamber with either an inlet or outlet blood conduit.

Broadly speaking, diaphragm pumps are old in the carburetor and fuel pump arts. Flexible diaphragms have been used in fuel pumps having two or more chambers for feeding fuel to carburetors and certain constructions have employed flapper valves integral with a flexible diaphragm for controlling the flow of gasoline to the carburetor. This type of pump employs changes in crankcase pressure as the source of power for actuating the diaphragm and relies on high speed revolutions of the engine, between about two thousand and nine thousand revolutions per minute, to actuate the diaphragm at the same rate. Apparatus of this type is shown in U.S. Pat. Nos. 2,769,838, 3,045,605 and 3,250,224. These constructions are multiple chamber devices having a flexible diaphragm equipped with integral flapper valves having wide, high-momentum and high resistance hinge regions that flap at high speeds as the gasoline is fed to the carburetor. Such devices are unsuitable for use with blood because blood would be destroyed by hemolysis if pumped through such a device.

A single chamber fuel pump using a flexible diaphram which employs flap valves that are restrained by a web finger which restrains the flap from separating substantially or freely from the plane of the diaphragm and causes the fluid to pass through a small annular passageway is shown in U.S. Pat. No. 2,980,032. This construction is also unsuitable for pumping blood due to hemolysis that would result from the sharp directional changes and tortuous path flow that would result from its use. This type of flow is to be contrasted with the smooth, substantially unidirectional flow that occurs through the freely openable, low inertia, unrestrained flapper valves in the diaphragm of the blood pump of this invention.

Another type of diaphragm pump for use in intravenous delivery of fluids is shown in U.S. Pat. Nos. 3,976,402 and 4,165,208. These pumps employ a flexible diaphragm as a germ barrier sheath for a piston which reciprocates into and from a liquid supply chamber to cause float or gravity controlled valves to allow liquid to pass from the supply chamber to a delivery chamber equipped with similar valves.

The above described devices represent the most pertinent prior art known to applicant. Prior to the present invention, applicant is unaware of any blood pump using a single chamber equipped with a flexible diaphragm having integral low inertia, freely openable and closable flapper valves of the type employed in the pump of this invention.

SUMMARY OF THE INVENTION

The blood pump of this invention is a small, single blood chamber device provided with a flexible diaphragm which forms one side of a blood chamber and seals the upper and lower body members into a liquid tight blood chamber having integral, spaced apart inlet and outlet blood conduits. Portions of the diaphragm sealingly isolate the conduit portions from side portions of the centrally located diaphragm-covered opening in the lower body member. The diaphragm also provides integral flapper valves which overlie the upper end openings in the inlet and outlet conduits and these flapper valves are attached to the diaphragm by a single thin web which is located in line with the longitudinal axis and direction of flow of blood from the inlet conduit into the blood chamber and from the blood chamber into the outlet conduit. The inner walls of the blood conduits and the inner wall surfaces of the blood chamber are smooth, gently curving surfaces that are free of sharp edges, or projections extending into the path of blood flow through the pump. The low inertia flapper valves are associated with smoothly rounded flapper stops located so as to prevent overtravel of the free end of the flapper and to insure quick, easy, positive closure of the flapper portion over the conduit openings with each penetration of the diaphragm into, and withdrawal of the diaphragm from, the cavity within the blood chamber.

The pump is small and typically provides a generally circular blood chamber of about 1-2 inches in diameter and is fabricated from moldable, blood-compatible plastic and flexible diaphragm components that are inexpensive and easily formed into the pump assembly of this invention. In operation, preferably as an integral part of an artificial kidney of the type shown in U.S. Pat. No. 4,231,871, the diaphragm is flexed by a positively driven reciprocating piston means, preferably fixedly attached to the diaphragm, at a slow rate in the range of 50–200 reciprocations per minute to provide a low pulsation-sinusoidal pattern of flow of blood at a substantially constant rate from a patient's artery to an artificial kidney and back to the patient's vein. The pump gently propels blood without causing hemolysis, clotting, or degradation to an unsatisfactory, or clinically unacceptable, degree and in general is at least as protective to blood components as the long-used and clinically acceptable peristaltic type pumps.

BRIEF DESCRIPTION OF THE DRAWINGS

FIG. 3 is a cross-sectional view of the assembly of FIG. 2 taken along the lines of 3—3 of FIG. 2 and showing the upper and lower body members sealed into an assembly by the diaphragm interfitted therebetween.

FIG. 4 is a sectional view of the diaphragm-covered central portion of the pump of FIG. 2 and taken along the lines 4—4 thereof.

FIG. 5 is a sectional view of the outlet conduit showing the outlet flapper valve in closed position against the lower closure portion of the upper body member, and taken along the line 5—5 of FIG. 2.

FIG. 6 is a sectional view of the inlet conduit showing the inlet flapper valve in closed position against the closure portion of the upper surface of the lower body member and taken along the line 6—6 of FIG. 2.

FIG. 7 is a sectional view of the injection site located in the upper wall of the upper body member of FIG. 3 and taken along the line 7—7 of FIG. 2.

DESCRIPTION OF THE PREFERRED EMBODIMENT

Figure 8:
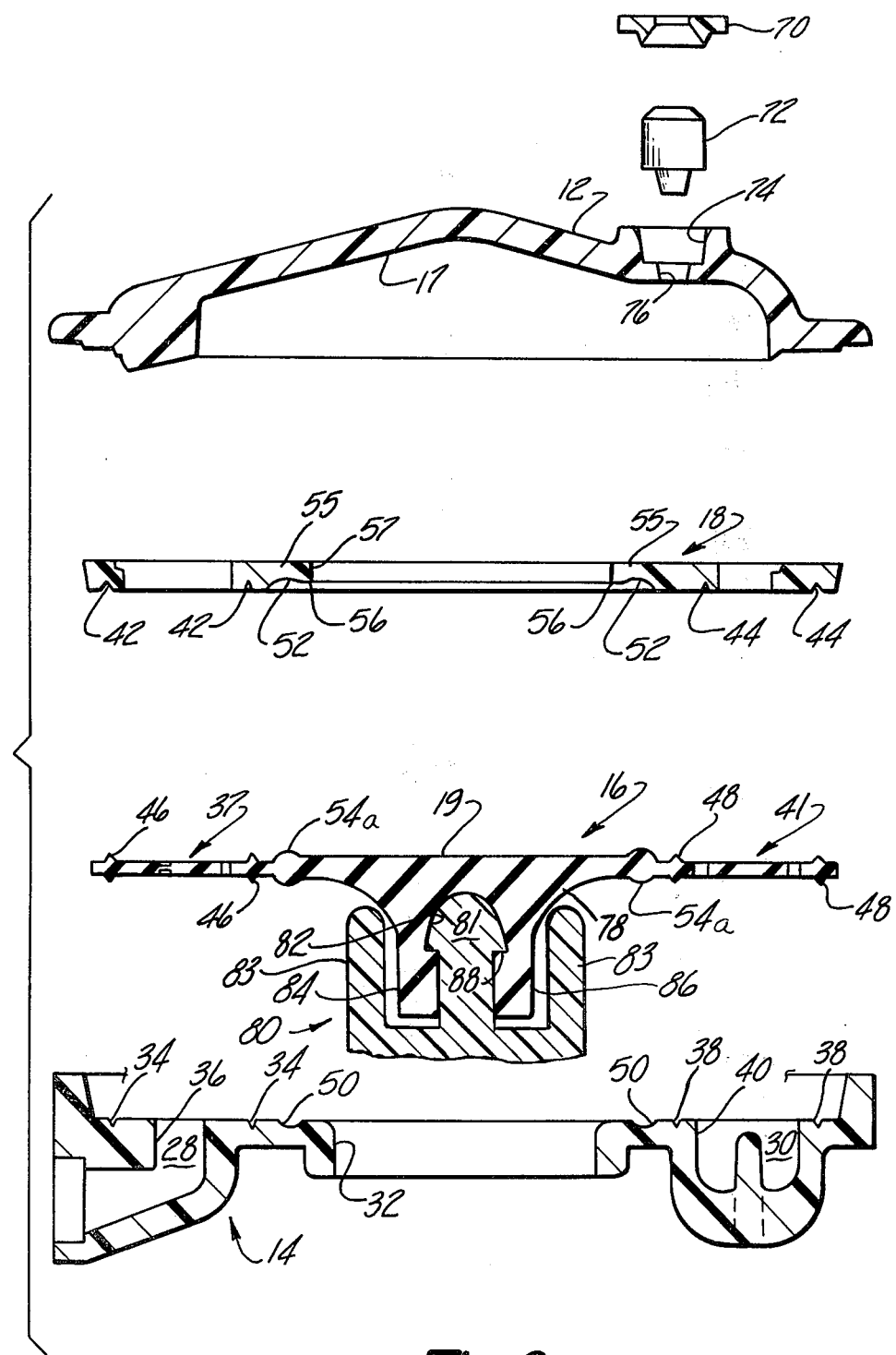
FIG. 8 is an exploded cross-sectional view of the cross-sectional assembly of FIG. 3 modified to include the preferred molded components and preformed diaphragm prior to assembly and including, from top to bottom, the injection site, upper body member, diaphragm securing ring, diaphragm shown with a preferred form of integral means for fixed attachment of a diaphragm reciprocator, and the lower body member.
Figure 9:
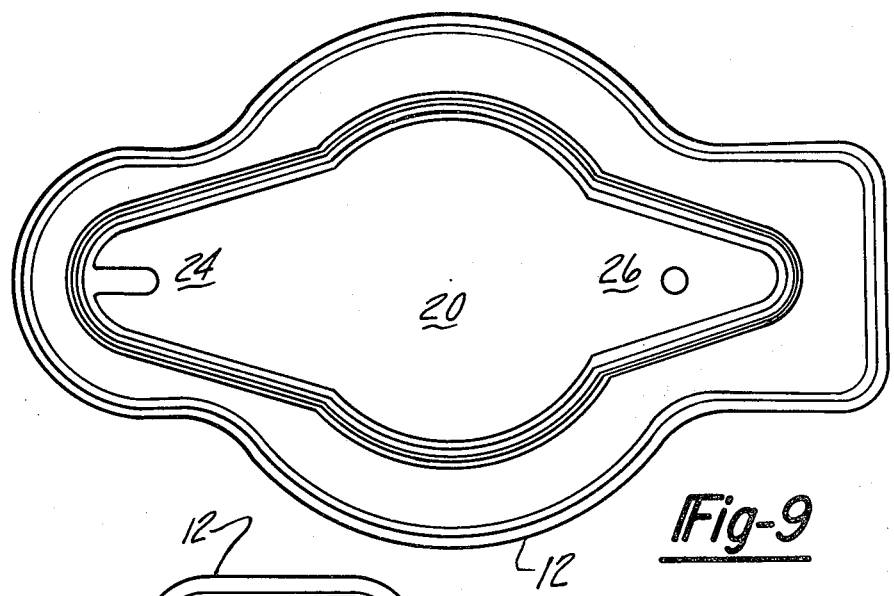
FIG. 9 is a view looking up at the inner surfaces in the upper body member seen in cross section in FIG. 8.
Figure 11:
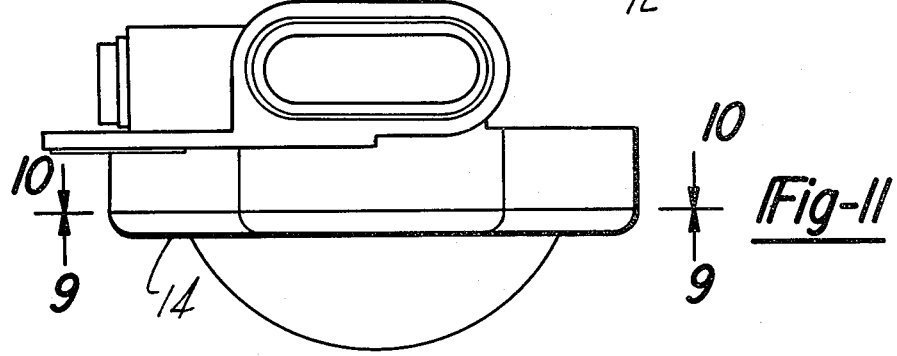
FIG. 11 is a bottom end view of the assembled pump of FIG. 2 oriented as in normal use position with the inlet blood conduit at the bottom and the outlet conduit at the top.
Figure 10:
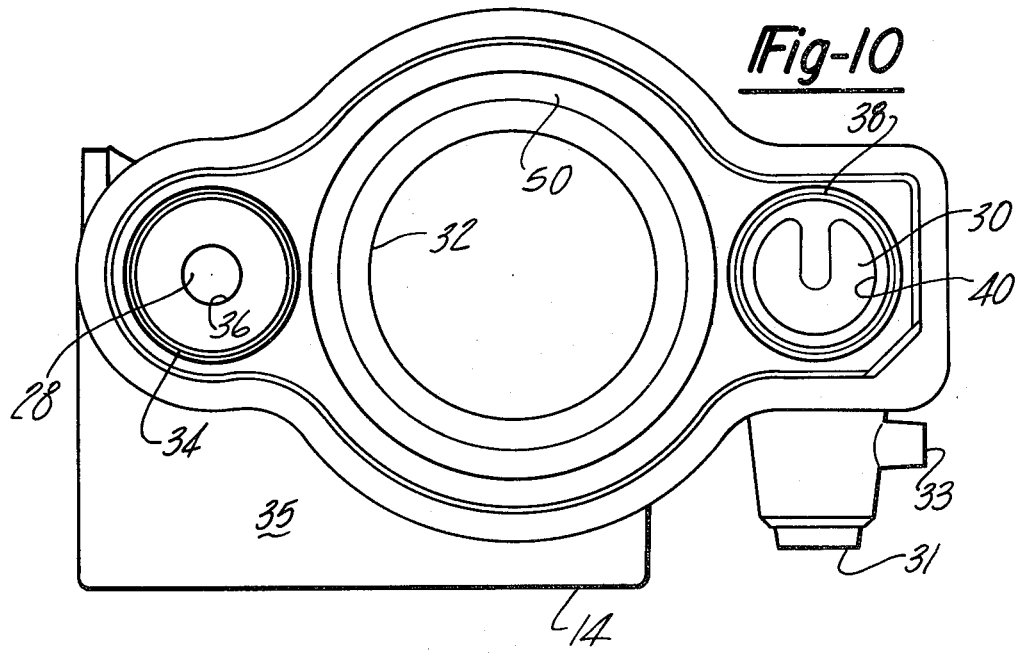
FIG. 10 is a view looking down at the top surfaces of the lower body member seen in cross section in FIG. 8 and modified for easy attachment to an artificial kidney.
Figure 12:
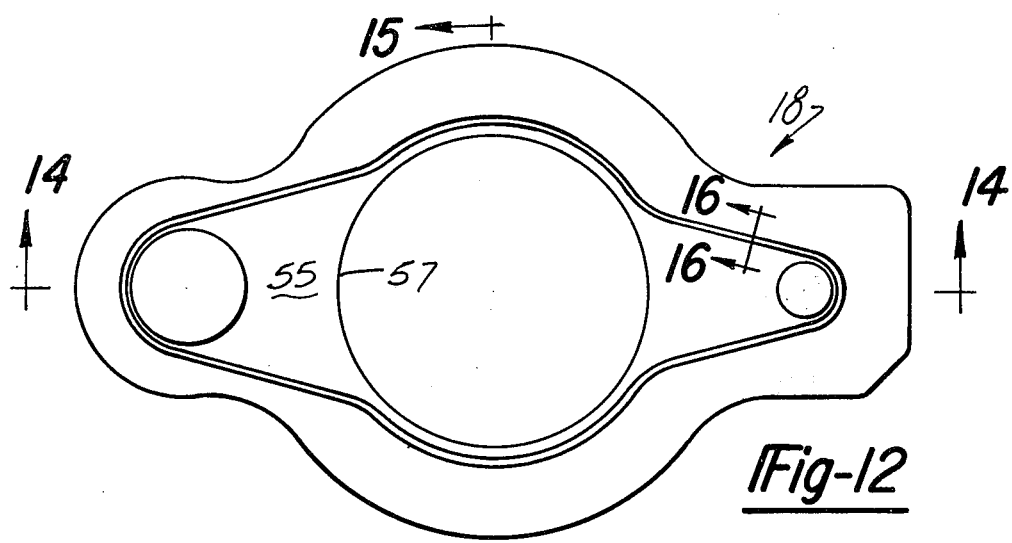
FIG. 12 is a top view of the diaphragm securing ring of FIG. 8.
Figure 13:
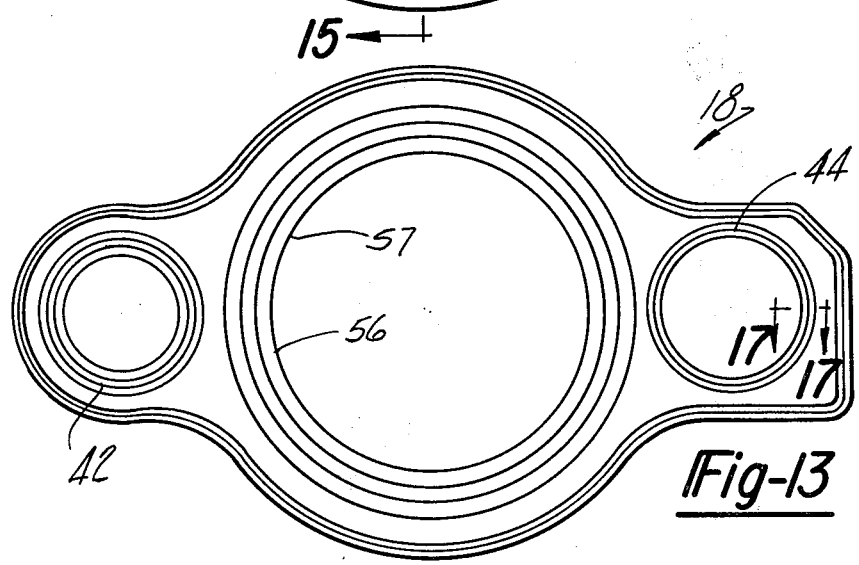
FIG. 13 is a bottom view of the diaphragm securing ring of FIG. 8.
Figure 14:
FIG. 14 is a cross-sectional view of the ring of FIG. 12 and taken along the line 14—14 thereof.
Figure 15:
FIG. 15 is a cross-sectional view of the ring of FIG. 12 and taken along the line 15—15 thereof.
Figure 16:
FIG. 16 is an enlargement of the attachment groove in the ring of FIG. 12 which joins the ring and upper body member into a single element upon sealing during assembly, taken along the line 16—16 thereof.
Figure 17:
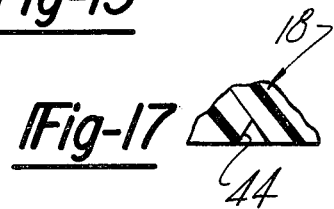
FIG. 17 is an enlargement of one of the grooves in the lower surface of the ring of FIG. 13 which mates with protrusions on the diaphragm of FIG. 8 to seal the upper and lower body members into a unit and to sealingly isolate the inlet and outlet conduits from the distensible central portion of the diaphragm.

The assembly generally designated 10 as shown in the drawings comprises a concave upper body housing 12, a lower body generally designated 14 and a flexible diaphragm and sealing member generally designated 16 that is interfitted and secured between the mating surfaces of the upper and lower body members as best seen in FIG. 3. The upper body is fabricated as two separate moldings, as shown in FIG. 8, and results from sealing the diaphragm support generally designated 18 to upper housing 12 along all mating edge surfaces to form an integral one-piece upper body as seen in FIG. 3. The lower body 14 comprises a single molding including an integral blood inlet conduit 28 and an outlet conduit 30 located on opposite sides of the diaphragm plunger opening 32, an administration site 33 for heparin injection or the like, and an attachment wing 35, or flange, for securing the assembly to an artificial kidney.

As assembled, blood cavity 20 is defined by the inner wall 17 of upper housing 12, the upper surfaces of diaphragm support 18 and the exposed upper surface 19 of diaphragm 16. Blood cavity 20 includes a centrally located hemispherical portion 22 having on one side an inlet portion 24 and on the other side an outlet portion 26, which side portions are adjacent to inlet conduit 28 and outlet conduit 30, respectively.

Diaphragm 16 is supported on and secured between the mating upper surface contact portions of lower body 14 and the lower surface contact surface portions of diaphragm support 18. As assembled, diaphragm 16 serves the dual functions of a diaphragm and sealing gasket to isolate inlet and outlet conduits 28, 30 from blood cavity 20 and from the central, distensible portion 19 of diaphragm 16 which overlies plunger opening 32 in lower body 14 and penetrates into blood cavity 20 from the solid line to the dotted line positions shown in FIG. 4.

As best seen in FIG. 8, lower body 14 is priovided on its upper surface with circular vee-shaped groove 34 which surrounds opening 36 at the upper end of inlet conduit 28, and with a similar vee-shaped groove 38 which surrounds opening 40 at the upper end of outlet conduit 30. The lower surface of diaphragm support 18, when assembled as the integral lower edge portion of upper body housing 12, presents vee-grooves 42, 44 which are located in vertical alignment with grooves 34, 38, respectively. The pairs of grooves 34, 42 and 38, 44 are sized to receive and form an interference, sealing fit with slightly larger vee-shaped protrusions 46, 48 on each surface of diaphragm 16. When diaphragm 16 is assembled as shown in FIG. 3, a liquid tight seal is thus formed which isolates blood cavity 20 from conduits 28, 30 except for operational communication, alternately, as the result of operation of integral flapper valves 37 and 41 as will be explained in more detail hereinafter.

The upper surface of lower body 14 is also provided with an arcuate groove 50 which is slightly larger in diameter than opening 32. Groove 50, together with opposing arcuate groove 52 in the lower surface of diaphragm support 18, upon assembly as shown in FIG.

3, sealingly engages and supports the slightly larger spherical protrusion 54A on diaphragm 16. The side portions of protrusion 54A extend outwardly from each surface of diaphragm 16 and have the cross-sectional shape of a truncated hemisphere.

As best seen in FIGS. 4 and 8, groove 52 in diaphragm support 18 is spaced slightly outwardly from the inner opening 57 defined by inwardly extending wall portion 55 of diaphragm support 18. Opening 57 is somewhat larger in diameter than opening 32 in lower body member 14 and wall 55 terminates on its lower surface in an abrupt radiused corner portion 56, preferably in the range of about 15° to 35° of the tangent to the radius from a vertical plane. As the distensible portion 19 of diaphragm 16 projects into cavity 20, corner portion 56 supportingly engages the upper contacting surface 19 and permits the diaphragm to distend in a smooth arc into cavity 20, as indicated by the dotted line portion illustrated in FIG. 4.

Figure 18:
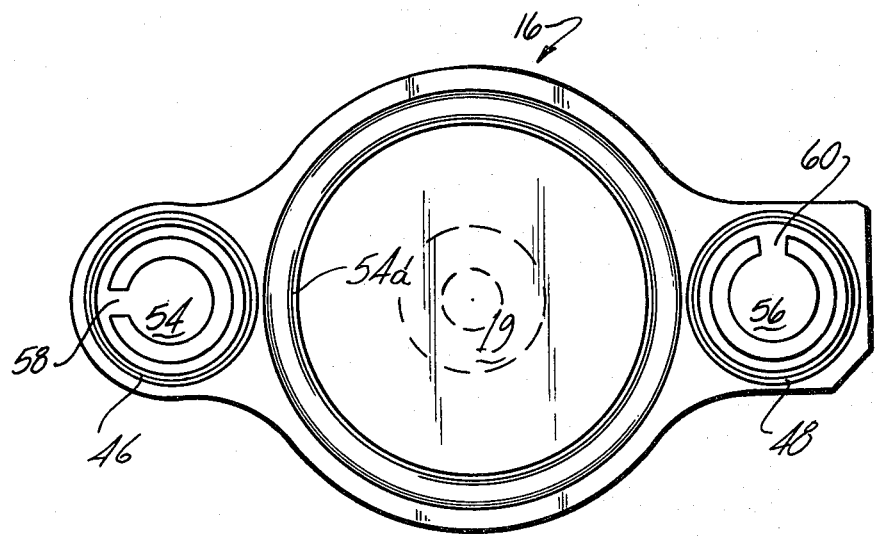
FIG. 18 is a top view of the diaphragm seal and flapper valve member of FIG. 3.

Flapper valves 37, 41, as best seen in FIG. 18, comprise circular flapper portions 54, 56, respectively, each of which is attached to diaphragm 16 by a web 58, 60, respectively.

Figure 19:
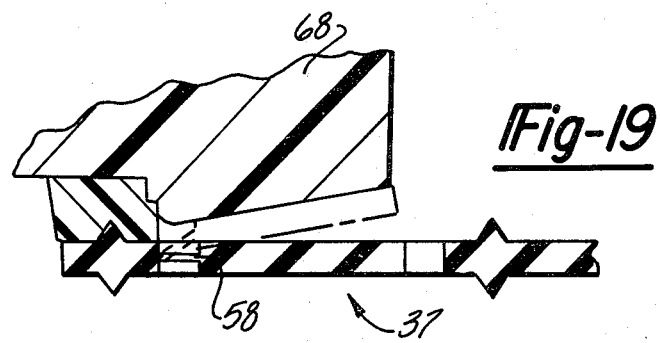
FIG. 19 is a cutaway enlargement of a section of the upper body member in the area of the inlet conduit at the left hand side of FIG. 3 and showing in dotted lines the flapper valve in open position against the stop located on the lower wall of the upper body member and in the central portion of the flapper valve opposite the single web attaching the flapper to the diaphragm.
Figure 20:
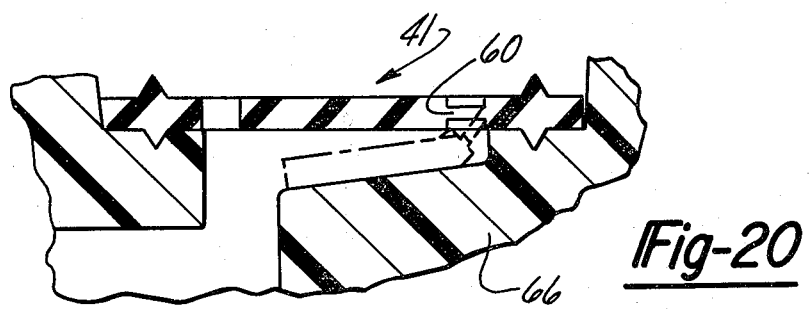
FIG. 20 is a cutaway enlargement of a section of the lower body member as seen in FIG. 5 and showing in dotted lines the flapper valve in open position against the stop in the center of the outlet conduit and attached to the diaphragm by a single web in line with the longitudinal axis of the outlet conduit.

Webs 58, 60 are thin relative to the diaphragm thickness and small relative to the size of the flapper portions 54, 56 and secure them to the diaphragm through a highly flexible pivot having low resistance to pivoting motion to open and close conduit openings 36, 40. Thus, flapper valves 37, 41 open and close in response to small forces due to blood flow, or minor pressure changes, at the instant of direction change in the reciprocation of diaphragm 16. Each web 58, 60 is located in line with, and on the center line of, the longitudinal axis of its associated blood conduit 28, 30, FIGS. 3, 5. This location of web 60 allows flapper portion 56 of flapper valve 41 to freely pivot and move from its closed position in contact with the lower peripheral closure surface 62 of upper body 12 surrounding outlet opening 40 of outlet conduit 30, FIG. 5, to its open position in contact with stop 66 as seen in FIG. 20. Similarly, the in-line location of web 58 allows flapper portion 54 to freely pivot and move, at the same instant, from its open position in contact with stop 68, FIG. 19, to its closed position in contact with upper peripheral closure surface 64 of lower body 14, FIG. 6.

Diaphragm 16 should be flexible, resistant to extension set, compatible with blood and have high fatigue resistance to repeated flexing. Silicone rubber is a preferred material from which to form a diaphragm, but other flexible polymeric materials such as ethylene-propylene rubbers are also satisfactory. The flexibility of the diaphragm will vary with thickness and diameter of opening 32 and, as an example, for silicone rubber may have a thickness of about 0.020 to 0.080 inches for a diameter of opening 32 of about 1 to 2 inches. A typical flapper 54, 56 may have a diameter of 3/16 to 5/16 inch and for a preferred diaphragm thickness of 0.040 inches the web is advantageously thinned to about 0.008 to 0.015 inch, preferably about 0.010 inch, with a web length of about three to six times its thickness, preferably about 0.05 inch. Flapper valve stops 66, 68 prevent excessive pivoting of flappers 41 and 37, to attain their open positions because of the relatively close location that leaves only a small space from the adjacent surface of the flapper when it is in its closed position. Such location nevertheless permits free, unrestrained blood flood through openings 40, 36 but concurrently insures easy, positive closure with only a slight degree of reversal of blood flow direction toward or from the flapper valve 37, 41. Stops 66, 68 are formed with smooth surfaces and present a gently curving projection from inner wall 17 and from the inner surface of outlet conduit 30, FIGS. 3, 5 and 6. Each stop 66, 68 is located so that when each of the flapper valves 41 and 37 is in its open position, the stops support flapper portions 56, 54 along the diametral plane which is in line with, and bisects, webs 60 and 58, respectively.

The blood pump of this invention is surprisingly small, light in weight, and relatively easily fabricated from three plastic molded parts and a resilient diaphragm. The pump size is surprising when it is considered that it pumps blood at the rate of 150 to 350 cubic centimeters per minute for four to six hour periods per hemodialysis treatment and is capable of use for more than one treatment. A number of moldable thermoplastic materials are suitable for use in making the pump. The most important requirements are blood compatibility, ease of molding and sealing, and low cost. It is desirable to employ a transparent or translucent material so that blood flow can be easily monitored and observed during use. Polystyrene is a preferred material. Other thermoplastic polymers such as acrylics or styreneacrylonitrile polymers are also satisfactory.

The preferred embodiments of styrene molded component elements which form the unitary assembly of this invention are shown in FIG. 8. During assembly, injection site cap 70 and rubber insert 72 are first positioned into injection site opening 74, which is provided with a smaller diameter central needle opening 76, and joined together, preferably by ultrasonic welding of cap 70 to upper body housing 12. Diaphragm support ring 18 is then positioned in contact with housing 12 and ultrasonically welded along the mating surfaces to form the integral upper body shown in FIG. 3. Diaphragm 16 is then positioned on lower body 14 and pressed into contact with the upper body assembly and ultrasonically sealed along all mating surface edges to form the pump assembly 10.

Diaphragm 16, illustrated in FIGS. 3 and 4, is desirably made from a selected rubber having sufficient resistance to extension set, or permanent stretching, to repetitively retract from its dotted line position to the solid line position shown in FIG. 4 due to its inherent resilience. Such diaphragms may be advanced into the blood cavity 20 by any suitable plunger or reciprocating piston, and preferably by a plunger having a diameter only slightly smaller than opening 32. When using a diaphragm with a non-integral plunger 39, FIG. 3, the preferred method of insuring consistant, repetitive, return of the diaphragm to the solid line position shown in FIG. 4 is to preload the diaphragm by forcing the plunger against the diaphragm to slightly distend the diaphragm into cavity 20. While the resiliency of the diaphragm controls the required degree of preloading, a few simple trials will easily establish the optimum conditions for each assembly. Pump assemblies employing preloaded diaphragms made of silicone rubber have been made that performed satisfactorily as blood pumps for use in hemodialysis treatments.

A preferred form of diaphragm 16 is illustrated in FIG. 8. The diaphragm shown there is modified to include integral attachment means 78 for disconnectably receiving a diaphragm plunger 80 to fixedly attach the reciprocating plunger to the diaphragm. This construction permits exact replication of length of stroke and resultant degree of penetration of the diaphragm into blood cavity 20 for each reciprocation and thus assures constant, steady expulsion of identical volumes of blood on each cycle. Accurate, steady, uniform rates of blood flow are thus attained merely by altering the length, or rate of reciprocation, of the plunger.

This preferred positive attachment of the plunger has the advantage of producing a wider, more uniform arc of penetration into blood cavity 20 which increases volume displacement of blood at lesser inward flexure distance at the center point of the plunger, thereby decreasing fatigue or localized stretching adjacent the end of the plunger.

The modified diaphragm shown in FIG. 8 is a one-piece molding of silicone rubber. The distensible portion 19 is increased in thickness relative to the outer flap supporting portion and on its lower side is provided with a molded extension 78 which includes a dart-shaped cavity 82 that is adapted to disconnectably receive a plunger of similar shape. Plunger 80, as shown in FIG. 8, is provided with a dart-shaped head portion 81, and annular shaped ring 83, which are attached to the diaphragm by forcibly inserting head portion 81 into cavity 82 by spreading wing portions 84, 86 apart as the forward curved edges of plunger head 81 is snapped into locking engagement under the inwardly extending flange portion 88 of cavity 82. It is to be understood that other positive attachment means may be used, including those having other shapes of plunger heads, receiving apertures therefor and other than resilient materials, if desired, since improved, positive operation on both the penetration and withdrawal strokes of the diaphragm is the preferred form of the invention.

Figure 1:
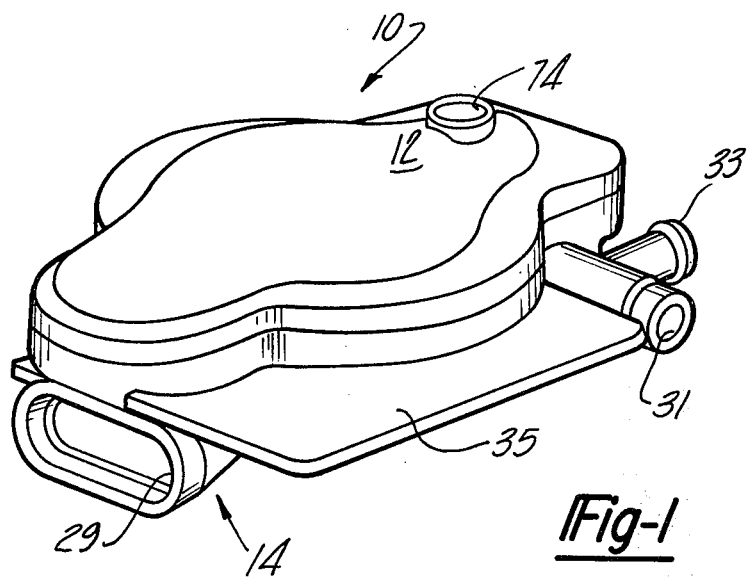
FIG. 1 is a perspective view of the pump assembly of the present invention.
Figure 2:
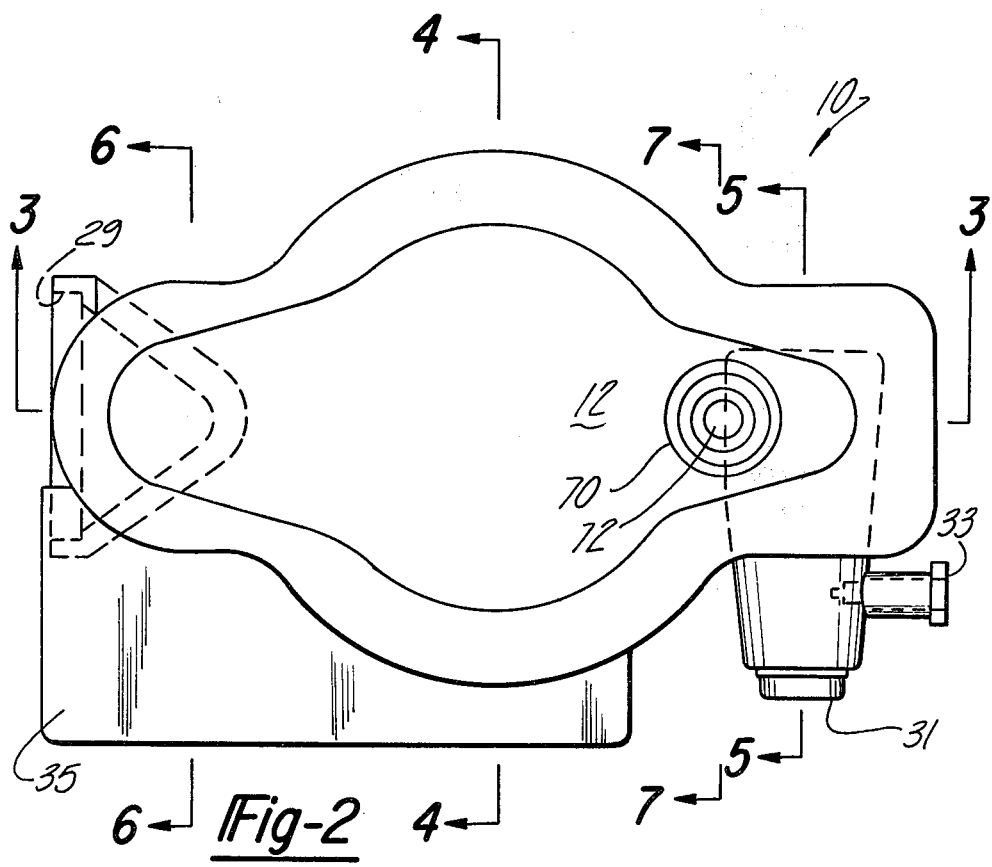
FIG. 2 is a top plan view of a preferred embodiment of the pump shown in FIG. 1.

Pump 10 is approximately 2 to 3 inches long, from bottom inlet conduit 28 to top outlet conduit 30. Inlet conduit 28 is substantially wider at its mouth portion 29 than at the upper end opening 36 into blood cavity 20, and gradually tapers inwardly and upwardly as shown in FIG. 2 and FIG. 3, to thereby serve as connecting means for attaching blood supply means or integral blood pressure measuring means, if desired. Outlet conduit 30 tapers smoothly from opening 40 to blood tube connector opening 31 and the inner walls of both tapering conduits are free from sharp projections in the path of blood flow to prevent swirling or dead spots that could cause hemolysis or clotting of the blood being pumped.

I claim:

1. A blood pump for medical use comprising body means defining a blood chamber portion, a plunger receiving opening, and inlet and outlet conditions; a diaphragm of resiliently flexible material extending across and sealing said opening from said chamber portion and cooperating with said chamber portion to define a blood chamber, said diaphragm being movable in a pumping action for alternately reducing and increasing the volume of said blood chamber; said inlet and outlet conduits communicating with said blood chamber; inlet and outlet flapper valves or resiliently yieldable flexible material associated with said inlet and outlet conduits respectively for alternately closing and opening the communication between said inlet conduit and chamber and simultaneously opening and closing the communication between said outlet conduit and chamber upon said pumping action of said diaphragm reducing and increasing said volume respectively; each flapper valve comprising a single element of resiliently yieldable flexible material having a disc portion, a fixed portion, and a web portion connecting said disc and fixed portions; the disc portion of each flapper valve overlying the opening of its associated conduit into said blood chamber and being sufficiently thick to resist collapsing into the latter opening in response to fluid pressure changes in said blood chamber during said pumping action, the fixed portion of each flapper valve having a thickness substantially equal to the thickness of the disc portion and being secured to said body means, and the web portion of each flapper valve being reduced in both width and thickness with respect to the disc portion to effect a highly flexible hinge facilitating alternate opening and closing hinge movement of the connected disc portion; and means for limiting opening hinge movement of each disc portion to a predetermined small angle comprising a separate ramp portion of said body means extending at said angle from adjacent to each web portion and in the downstream direction of fluid flow.

2. The combination according to claim 1, said diaphragm and inlet and outlet flapper valves comprising a single diaphragm member of said resiliently yieldable flexible material, said diaphragm having a thickness greater than the thickness of said flapper valves and having additionally thickened portions extending into said plunger receiving opening exteriorly of said blood chamber for connection with a reciprocal plunger.

3. The combination according to claim 2, said diaphragm member having an annular thickening around said plunger receiving opening and having separate annular thickenings around the openings of said inlet and outlet conduits into said blood chamber, and said body means having annular recesses mating with and receiving said annular thickenings respectively at interference fits and in sealing relationship for securing said thickenings in fixed positions with respect to said body means and for effecting fluid seals between said diaphragm member and body means around each of said openings.

4. The combination according to claim 3, said body means comprising a first body member defining said chamber portion, a second body member having said plunger receiving opening and said inlet and outlet conduits, and a diaphragm support, said diaphragm support and second body member having said annular recesses therein and clamping said diaphragm member therebetween, and said first body member clamping said diaphragm support toward said diaphragm member and second body member.

5. A blood pump for medical use comprising body means defining a blood chamber portion, a plunger receiving opening, and inlet and outlet conduits; a diaphragm of resiliently flexible material extending across and sealing said opening from said chamber portion and cooperating with said chamber portion to define a blood chamber, said diaphragm being movable in a pumping action for alternately reducing and increasing the volume of said blood chamber; said inlet and outlet conduits communicating with said blood chamber; inlet and outlet flapper valves of resiliently yieldable flexible material associated with said inlet and outlet conduits respectively for alternately closing and opening the communication between said inlet conduit and chamber and simultaneously opening and closing the communication between said outlet conduit and chamber upon said pumping action of said diaphragm reducing and increasing said volume respectively; each flapper valve comprising a single element of resiliently yieldable flexible material having a disc portion, a fixed portion, and a web portion connecting said disc and fixed portions, the disc portion of each flapper valve overlying the opening of its associated conduit into said blood chamber and being sufficiently thick to resist collapsing into the latter opening in response to fluid pressure changes in said blood chamber during said pumping action, the fixed portion of each flapper valve having a thickness substantially equal to the thickness of the disc portion and being secured to said body means, and the web portion of each flapper valve being reduced in both width and thickness with respect to the disc portion to effect a highly flexible hinge facilitating alternate opening and closing hinge movement of the connected disc portion; said diaphragm and inlet and outlet flapper valves comprising a single flexible diaphragm member of said resiliently yieldable flexible material, said diaphragm having a thickness greater than the thickness of said flapper valves and having additionally thickened portions extending into said plunger receiving opening exteriorly of said blood chamber for connection with a reciprocal plunger.

6. The combination according to claim 5, said diaphragm member having an annular thickening around said plunger receiving opening and having separate annular thickenings around the openings of said inlet and outlet conduits into said blood chamber, and said body means having annular recesses mating with and receiving said annular thickenings respectively at interference fits and in sealing relationship for securing said thickenings in fixed positions with respect to said body means and for effecting seals between said diaphragm member and body means around each of said openings.

7. The combination according to claim 6, said body means comprising a first body member defining said chamber portion, a second body member having said plunger receiving opening and said inlet and outlet conduits, and a diaphragm support, said diaphragm support and second body member having said annular recesses therein and clamping said diaphragm member therebetween, and said first body member clamping said diaphragm support toward said diaphragm member and second body member.

8. A blood pump for medical use comprising body means defining a blood chamber portion, a plunger receiving opening, and inlet and outlet conduits; a diaphragm of resiliently flexible material extending across and sealing said opening from said chamber portion and cooperating with said chamber portion to define a blood chamber, said diaphragm being movable in a pumping action for alternately reducing and increasing the volume of said blood chamber; said inlet and outlet conduits communicating with said blood chamber; inlet and outlet flapper valves of resiliently yieldable flexible material associated with said inlet and outlet conduits respectively for alternately closing and opening the communication between said inlet conduit and chamber and simultaneously opening and closing the communication between said outlet conduit and chamber upon said pumping action of said diaphragm reducing and increasing said volume respectively; each flapper valve comprising a single element of resiliently yieldable flexible material having a disc portion, a fixed portion, and a web portion connecting said disc and fixed portions; the disc portion of each flapper valve overlying the opening of its associated conduit into said blood chamber and being sufficiently thick to resist collapsing into the latter opening in response to fluid pressure changes in said blood chamber during said pumping action, the fixed portion of each flapper valve having a thickness substantially equal to the thickness of the disc portion and being secured to said body means, and the web portion of each flapper valve having a reduced cross sectional area with respect to the disc portion to effect a highly flexible hinge facilitating alternate opening and closing hinge movement of the connected disc portion; said diaphragm and inlet and outlet flapper valves comprising a single diaphragm member of said resiliently yieldable flexible material, said diaphragm having a thickness greater than the thickness of said flapper valves and having additionally thickened portions extending into said plunger receiving opening exteriorly of said blood chamber for connection with a reciprocal plunger; said diaphragm member having an annular thickening around said plunger receiving opening and having separate annular thickenings around the openings of said inlet and outlet conduits into said blood chamber, and said body means having annular recesses mating with and receiving said annular thickenings respectively at interference fits and in sealing relationship for securing said thickenings in fixed positions with respect to said body means and for effecting fluid seals between said diaphragm member and body means around each of said openings.

9. The combination according to claim 1, said body means comprising a first body member defining said chamber portion, a second body member having said plunger receiving opening and said inlet and outlet conduits, and a diaphragm support, said diaphragm support and second body member having said annular recesses therein and clamping said diaphragm member therebetween, and said first body member clamping said diaphragm support toward said diaphragm member and second body member.

* * * * *